(12) United States Patent
Richards-Kortum et al.

(10) Patent No.: US 7,499,161 B2
(45) Date of Patent: Mar. 3, 2009

(54) DEPTH-RESOLVED SPECTROSCOPY METHOD AND APPARATUS

(75) Inventors: Rebecca Richards-Kortum, Austin, TX (US); Richard A. Schwarz, Houston, TX (US); Ann M. Gillenwater, Pearland, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 168 days.

(21) Appl. No.: 11/428,806

(22) Filed: Jul. 5, 2006

(65) Prior Publication Data

US 2007/0038120 A1 Feb. 15, 2007

Related U.S. Application Data

(60) Provisional application No. 60/696,655, filed on Jul. 5, 2005.

(51) Int. Cl.
    *G01J 3/30* (2006.01)
(52) U.S. Cl. ..................................... 356/317
(58) Field of Classification Search ................. 356/432, 356/317, 326; 359/664
See application file for complete search history.

(56) References Cited

U.S. PATENT DOCUMENTS

| | | | |
|---|---|---|---|
| 5,201,318 A | 4/1993 | Rava et al. | 600/476 |
| 5,205,291 A | 4/1993 | Petter | 600/431 |
| 5,345,941 A | 9/1994 | Rava et al. | 600/476 |
| 5,419,323 A | 5/1995 | Kittrell et al. | 600/476 |
| 5,421,337 A | 6/1995 | Richards-Kortum et al. | 600/477 |
| 5,421,339 A | 6/1995 | Ramanujam | 600/477 |
| 5,562,100 A | 10/1996 | Kittrell et al. | 600/476 |
| 5,612,540 A | 3/1997 | Richards-Kortum et al. | 250/461.2 |
| 5,623,932 A | 4/1997 | Ramanujam et al. | 600/317 |
| 5,697,373 A | 12/1997 | Richards-Kortum et al. | 600/475 |
| 5,699,795 A | 12/1997 | Richards-Kortum et al. | 600/478 |
| 5,842,995 A | 12/1998 | Mahadevan-Jansen et al. | 600/473 |
| 5,920,399 A | 7/1999 | Sandison et al. | 356/418 |
| 5,929,985 A | 7/1999 | Sandison et al. | 356/318 |
| 5,953,477 A * | 9/1999 | Wach et al. | 385/115 |
| 5,991,653 A | 11/1999 | Richards-Kortum et al. | 600/475 |

(Continued)

FOREIGN PATENT DOCUMENTS

| | | |
|---|---|---|
| WO | WO 00/42906 | 7/2000 |
| WO | WO 2005/031291 | 4/2005 |

OTHER PUBLICATIONS

Schwarz et al., "Ball lens coupled fiber-optic probe for depth-resolved spectroscopy of epithelial tissue," *Optics Letters*, 30:1159-1161, 2005.
International Search Report and Written Opinion mailed Apr. 27, 2007.

*Primary Examiner*—Kara E Geisel
(74) *Attorney, Agent, or Firm*—Fulbright & Jaworski L.L.P.

(57) ABSTRACT

Methods and apparatus for depth-resolved spectroscopy. A ball lens may be used to redirect light from a fiber-optic probe so that the light intersects the detection region of a collection probe in a specific depth layer of the specimen. A fiber-optic probe may comprise a collection fiber proximal to a central axis of a ball lens and a pair of illumination fibers distal to the central axis.

22 Claims, 7 Drawing Sheets

U.S. PATENT DOCUMENTS

| | | | |
|---|---|---|---|
| 6,095,982 A | 8/2000 | Richards-Kortum et al. | 600/476 |
| 6,135,965 A | 10/2000 | Tumer et al. | 600/476 |
| 6,144,791 A * | 11/2000 | Wach et al. | 385/123 |
| 6,174,424 B1 * | 1/2001 | Wach et al. | 205/73 |
| 6,187,289 B1 | 2/2001 | Richards-Kortum et al. | 424/9.8 |
| 6,222,970 B1 * | 4/2001 | Wach et al. | 385/115 |
| 6,241,662 B1 | 6/2001 | Richards-Kortum et al. | 600/310 |
| 6,258,576 B1 | 7/2001 | Richards-Kortum et al. | 435/40.52 |
| 6,366,726 B1 * | 4/2002 | Wach et al. | 385/115 |
| 6,370,406 B1 * | 4/2002 | Wach et al. | 600/310 |
| 6,370,422 B1 | 4/2002 | Richards-Kortum et al. | 600/478 |
| 6,416,234 B1 * | 7/2002 | Wach et al. | 385/70 |
| 6,487,349 B2 * | 11/2002 | Wach et al. | 385/115 |
| 6,571,118 B1 | 5/2003 | Utzinger et al. | 600/476 |
| 6,593,101 B2 | 7/2003 | Richards-Kortum et al. | 435/29 |
| 6,608,671 B2 * | 8/2003 | Tsien et al. | 356/72 |
| 6,639,674 B2 | 10/2003 | Sokolov et al. | 356/369 |
| 6,697,666 B1 | 2/2004 | Richards-Kortum et al. | 600/478 |
| 6,766,184 B2 | 7/2004 | Utzinger | 600/407 |
| 7,002,671 B2 * | 2/2006 | Tsien et al. | 356/72 |
| 7,142,290 B2 * | 11/2006 | Tsien et al. | 356/72 |
| 2001/0055462 A1 | 12/2001 | Seibel | 385/147 |
| 2002/0065468 A1 | 5/2002 | Urtzinger et al. | 600/476 |
| 2002/0127632 A1 | 9/2002 | Richards-Kortum et al. | 435/40.51 |
| 2002/0135752 A1 | 9/2002 | Sokolov et al. | 356/39 |
| 2003/0103262 A1 | 6/2003 | Descour et al. | 359/368 |
| 2003/0191398 A1 | 10/2003 | Motz et al. | 600/478 |
| 2004/0023415 A1 | 2/2004 | Sokolov et al. | 436/518 |
| 2004/0064053 A1 | 4/2004 | Chang et al. | 600/478 |
| 2004/0073120 A1 * | 4/2004 | Motz et al. | 600/478 |
| 2004/0162489 A1 | 8/2004 | Richards-Kortum et al. | 600/473 |
| 2005/0080343 A1 | 4/2005 | Richards-Kortum et al. | 600/476 |
| 2006/0058611 A1 | 3/2006 | Descour et al. | 600/407 |

* cited by examiner

DEPTH-RESOLVED SPECTROSCOPY METHOD AND APPARATUS

CROSS-REFERENCE TO RELATED APPLICATIONS

This application claims priority to U.S. Provisional Patent Application Ser. No. 60/696,655, filed on Jul. 5, 2005, the entire text of which is specifically incorporated by reference herein without disclaimer.

BACKGROUND OF THE INVENTION

1. Field of the Invention

Embodiments of the present invention relate generally to optical spectroscopy. More particularly, embodiments of the present invention relate to depth-resolved measurements of fluorescence and reflectance properties of a specimen.

2. Description of Related Art

Optical spectroscopy is emerging as an effective diagnostic technique for noninvasive detection of cancers and prefacers that originate in the epithelial lining of organs such as the uterine cervix, the oral cavity, the urinary bladder, and the esophagus. The progression of precancer in these tissues produces morphologic and biochemical changes in the epithelium and supporting stroma. These changes include alterations in epithelial cell morphology and metabolic activity, changes in stromal protein morphology and cross-linking, and increasing stromal angiogenesis. As a result, the concentration and distribution of endogenous fluorophores such as reduced nicotinamideadenine dinucleotide, flavin adenine dinucleotide, keratin, tryptophan, and collagen cross-links, and absorbers such as hemoglobin, are altered with the progression of precancer. Thus, knowledge of the depth-dependent distribution of chromophores may have important diagnostic significance.

Endogenous chromophores can be detected noninvasively in vivo by use of fiber-optic fluorescence and reflectance spectroscopy. Many fiber-optic probe designs collect the integrated signal from both the epithelium (which is typically of the order of 300 µm thick) and the underlying stroma. In these systems, sophisticated analysis strategies are required for deconvolution of spectroscopic data to yield quantitative concentrations of chromophores, and little information about depth-related changes is obtained. Fiber-optic probes that can localize spectroscopic information by depth to distinguish epithelial and stromal optical signatures should improve the ability of spectroscopy to evaluate noninvasively the progression of precancerous changes.

A variety of probe designs for obtaining localized or depth-resolved spectroscopic data have been reported. Single-fiber probe configurations, in which the same fiber is used for illumination and collection, are sensitive to light scattering from superficial tissue regions. However, the use of single-fiber probes for optical measurements is limited by lower signal-to-noise ratios that are due to autofluorescence generated by impurities in the fiber core and by specular reflection from fiber surfaces. With multiple-fiber probes, many configurations are possible. Straight-fiber geometries with different source detector separations permit some depth discrimination; however, in epithelial tissue the signal from the stroma tends to dominate, even at minimum source-detector separation. Angled illumination and collection fibers can be used to target specific depth regions. Targeting the epithelial layer, however, requires steep angles that may increase the diameter of the probe so as to be impractical for clinical probe designs.

It is therefore desirable to obtain depth-resolved spectroscopic data without the associated limitations noted in previous designs. Referenced shortcomings of conventional methodologies and apparatus mentioned above are not intended to be exhaustive, but rather are among several that tend to impair the effectiveness of previously known techniques concerning optical spectroscopy. Other noteworthy problems may also exist; however, those mentioned here are sufficient to demonstrate that methodology and apparatus appearing in the art have not been altogether satisfactory and that a significant need exists for the techniques and apparatus described and claimed here.

SUMMARY OF THE INVENTION

Embodiments of the present disclosure provide a method and apparatus for depth-resolved spectroscopy of a specimen. Embodiments comprise a method of obtaining spectroscopic data using a fiber-optic probe comprising an excitation source, a collection fiber and a ball lens to redirect the light from the excitation source. The light is redirected so that it intersects a detection region of the collection fiber in a specific depth layer. The light illuminates a target, which generates an optical signal that is received by the collection fiber.

In certain embodiments of the present disclosure, the fiber-optic probe comprises a pair of excitation fibers equidistant from a collection fiber that is proximal to a central axis of the ball lens.

As used herein, "ball-shaped lens" or "ball lens" refers to any lens that is substantially spherical in shape.

As used herein, the terms "a" and "an" are defined as one or more unless this disclosure explicitly requires otherwise.

The term "substantially" and its variations are defined as being largely but not necessarily wholly what is specified as understood by one of ordinary skill in the art, and in one non-limiting embodiment the term "substantially" refers to ranges within 10%, preferably within 5%, more preferably within 1%, and most preferably within 0.5% of what is specified.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements possesses those one or more steps or elements, but is not limited to possessing only those one or more elements. Likewise, a step of a method or an element of a device that "comprises," "has," "includes" or "contains" one or more features possesses those one or more features, but is not limited to possessing only those one or more features. Furthermore, a device or structure that is configured in a certain way is configured in at least that way, but may also be configured in ways that are not listed.

The term "coupled," as used herein, is defined as connected, although not necessarily directly, and not necessarily mechanically Other features and associated advantages will become apparent with reference to the following detailed description of specific, example embodiments in connection with the accompanying drawings.

BRIEF DESCRIPTION OF THE DRAWINGS

The following drawings form part of the present specification and are included to further demonstrate certain aspects of the invention. The invention may be better understood by reference to one or more of these drawings in combination with the detailed description of example embodiments presented here. The drawings are not to scale, and certain distances or spacings may be exaggerated to provide clarity. The drawings are examples only. They do not limit the claims.

DESCRIPTION OF ILLUSTRATIVE EMBODIMENTS

Embodiments of this disclosure provide a method and apparatus for obtaining depth-dependent spectrographic data from targets distributed throughout a specimen.

Figure 1:
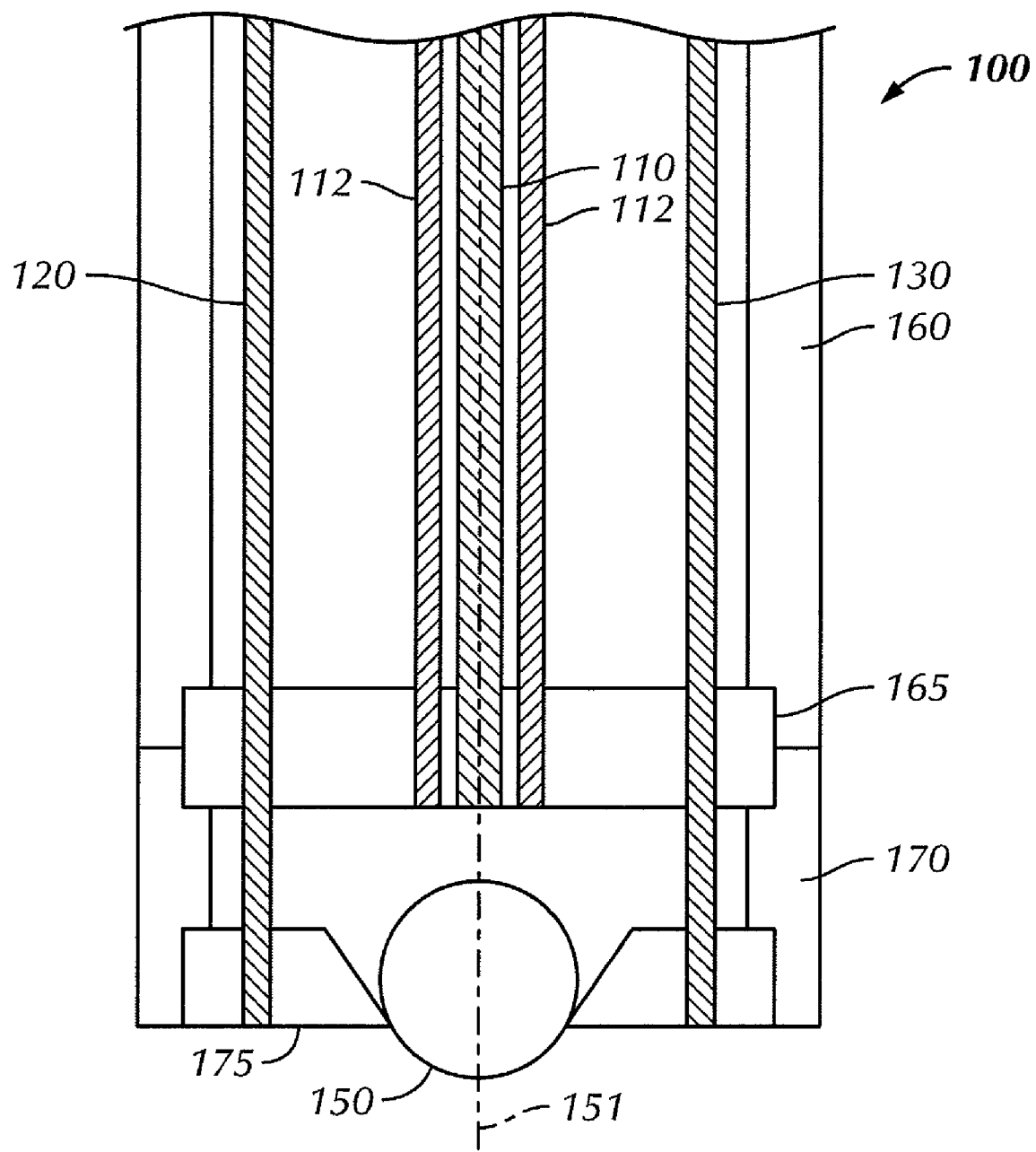
FIG. 1 is a section side view, in accordance with embodiments of this disclosure.
Figure 2:
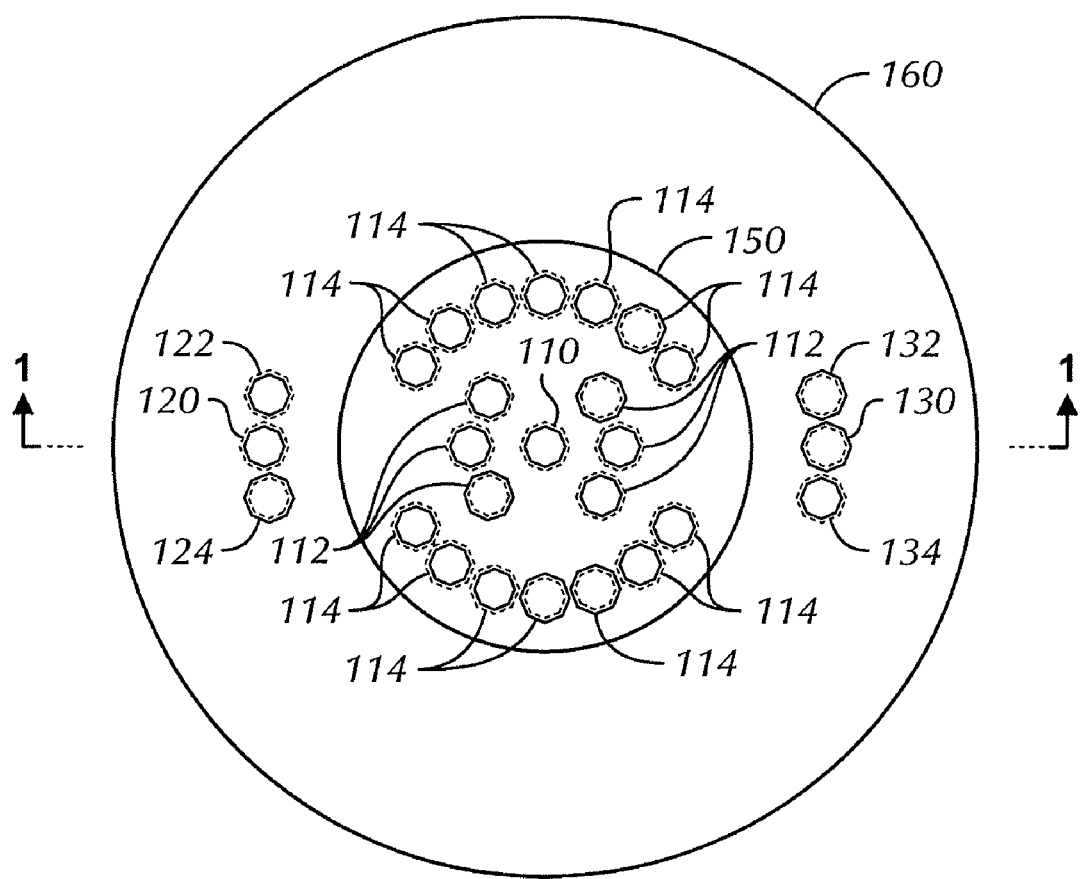
FIG. 2 is an end view, in accordance with embodiments of this disclosure.

FIG. 1 is a cross-section side view (taken along line 1-1 in FIG. 2) of a fiber-optic probe 100 in accordance with embodiments of this disclosure. FIG. 2 is a end view of probe 100, with certain components omitted for clarity (discussed more fully below). Fiber-optic probe 100 comprises a central collection fiber 110, a pair of deep tissue collection fibers 120, 130, and a generally spherical ball or ball-shaped lens 150. Distributed around central collection fiber 110 are a plurality of medium tissue illumination fibers 112 and a plurality of shallow tissue illumination fibers 114. Located adjacent to deep tissue collection fiber 120 are a pair of deep tissue illumination fibers 122, 124 and adjacent to deep tissue collection fiber 130 are a pair of deep tissue illumination fibers 132, 134. A sheath 160 encases the collection and illumination fibers and terminates at a plate 165. An extension member 170 extends beyond plate 165 and is coupled to a retaining member 175, which retains ball-shaped lens 150.

As shown in FIG. 1, central collection fiber 110 and medium illumination fibers 112 terminate at plate 165. However, deep tissue collection fibers 120, 130 and deep tissue illumination fibers 122, 124, 132 and 134 extend through plate 165 and terminate at retaining member 175. Ball-shaped lens 150 is secured to retaining member 175 (via epoxy or other suitable means) and is located proximal to the ends of central collection fiber 110, medium tissue illumination fibers 112 and shallow tissue illumination fibers 114. In certain embodiments ball-shaped lens 150 is a 2.0 millimeter diameter sapphire lens. Retaining member 175, extension member 170 and plate 165 are not shown in FIG. 2 for purposes of clarity.

Figure 3:
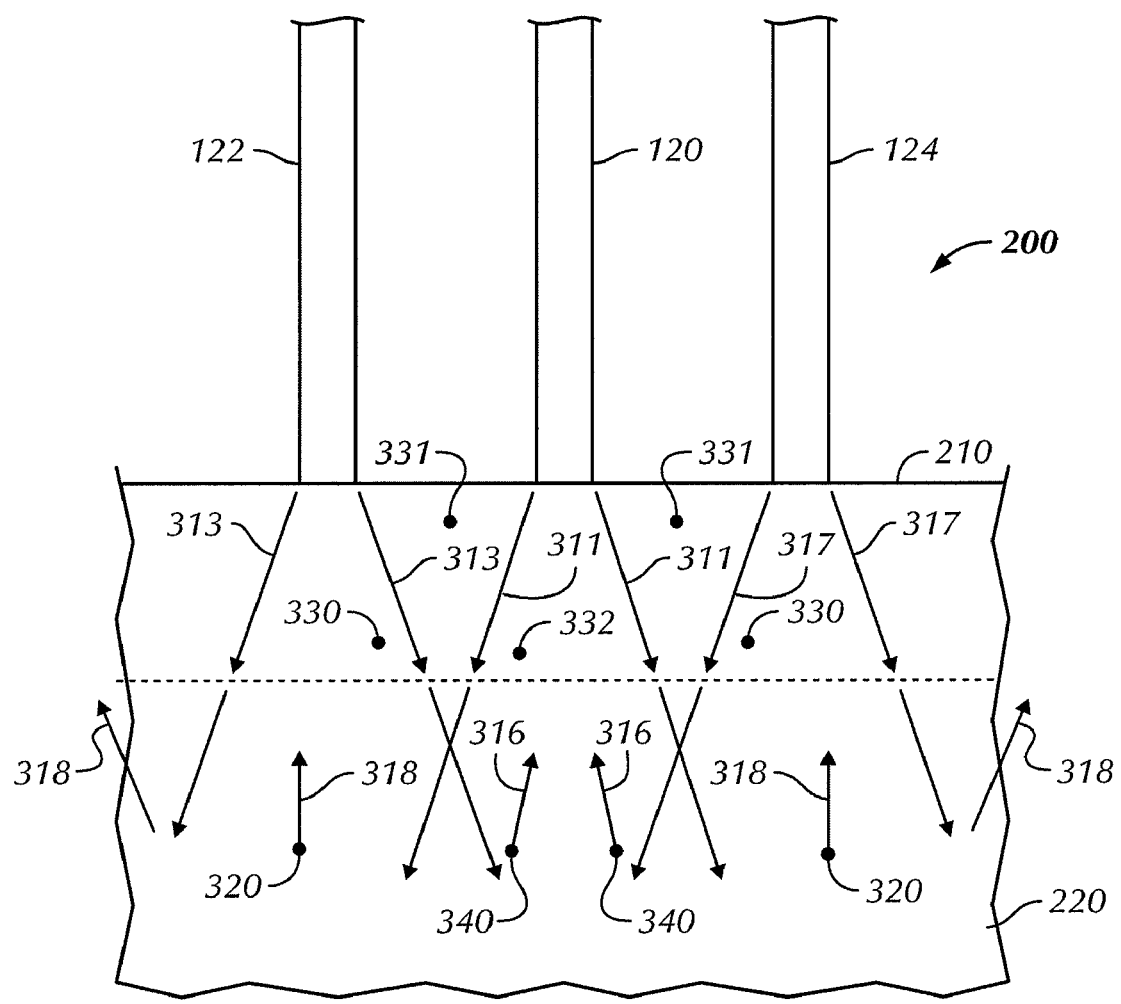
FIG. 3 is a detailed view of a fiber-optic probe, in accordance with embodiments of this disclosure.

Referring now to FIG. 3, deep tissue collection fiber 120 and illumination fibers 122, 124 (which are not refracted by ball-shaped lens 150) are shown. The general operating principles of fiber-optic probes are well-known and will not be discussed in detail in this disclosure. For an overview of such principles, see U. Utzinger and R. Richards-Kortum, "Fiber Optic Probes for Biomedical Optical Spectroscopy," Journal of Biomedical Optics 8(1), 121-147 (January 2003), herein incorporated by reference. FIG. 3 provides a detailed view of the ends of a deep tissue collection fiber 120 and illumination fibers 122, 124 in contact with or coupled with a specimen 200, which comprises a top layer 210 and a supporting layer 220. During operation, illumination fibers 122 and 124 emit light rays 313 and 317 that illuminate specimen 200. Specimen 200 comprises targets 340 in supporting layer 220 that are located within a detection region or cone 311 of collection fiber 120 and targets 320 in supporting layer 220 that are outside of detection cone 311. Light rays 313 and 317 are received by targets 320 and 340, which remit light rays 318 and 316, respectively. Specimen 200 also comprises targets 330, 331 and 332 in top layer 210. Targets 330 are illuminated by fibers 122, 124, while targets 332 are in detection cone 311. Targets 331 do not lie within detection cone 311 and are not illuminated by fibers 122, 124.

Remitted light rays 318 are outside a detection region or cone 311 of collection fiber 120, while remitted light rays 316 are inside detection cone 311. Detection cone 311 is a generally cone-shaped volume of space extending from the end of collection fiber 120 in which collection fiber 120 is capable of detecting light rays. As used in this disclosure, "remitted" light rays include light rays reflected or fluoresced from a specimen as a result of illuminating the specimen with an illumination or excitation light ray. Collection fiber 120 detects remitted light rays 316 that are within detection cone 311 and remitted light rays 316 are then transmitted to a spectrograph (not shown) for analysis. As shown in FIG. 3, light rays 313 and 317 do not intersect detection cone 311 in top layer 210. Therefore, any targets 330 in top layer 210 will be illuminated, but will not be detected. Similarly, targets 332 are in detection cone 311, but will not be illuminated. Targets 331 will be neither illuminated nor detected. Although the spacing of collection fiber 120 and illumination fibers 122, 124 could be reduced so that some targets 330 in top layer 210 could be illuminated and detected, the majority of targets that will be illuminated and detected are those below top layer 210. Conventional fiber-optic probe arrangements (such as deep tissue collection fiber 120 and illumination fibers 122, 124) are therefore not suited for illuminating and detecting targets near the surface of a specimen.

Figure 4:
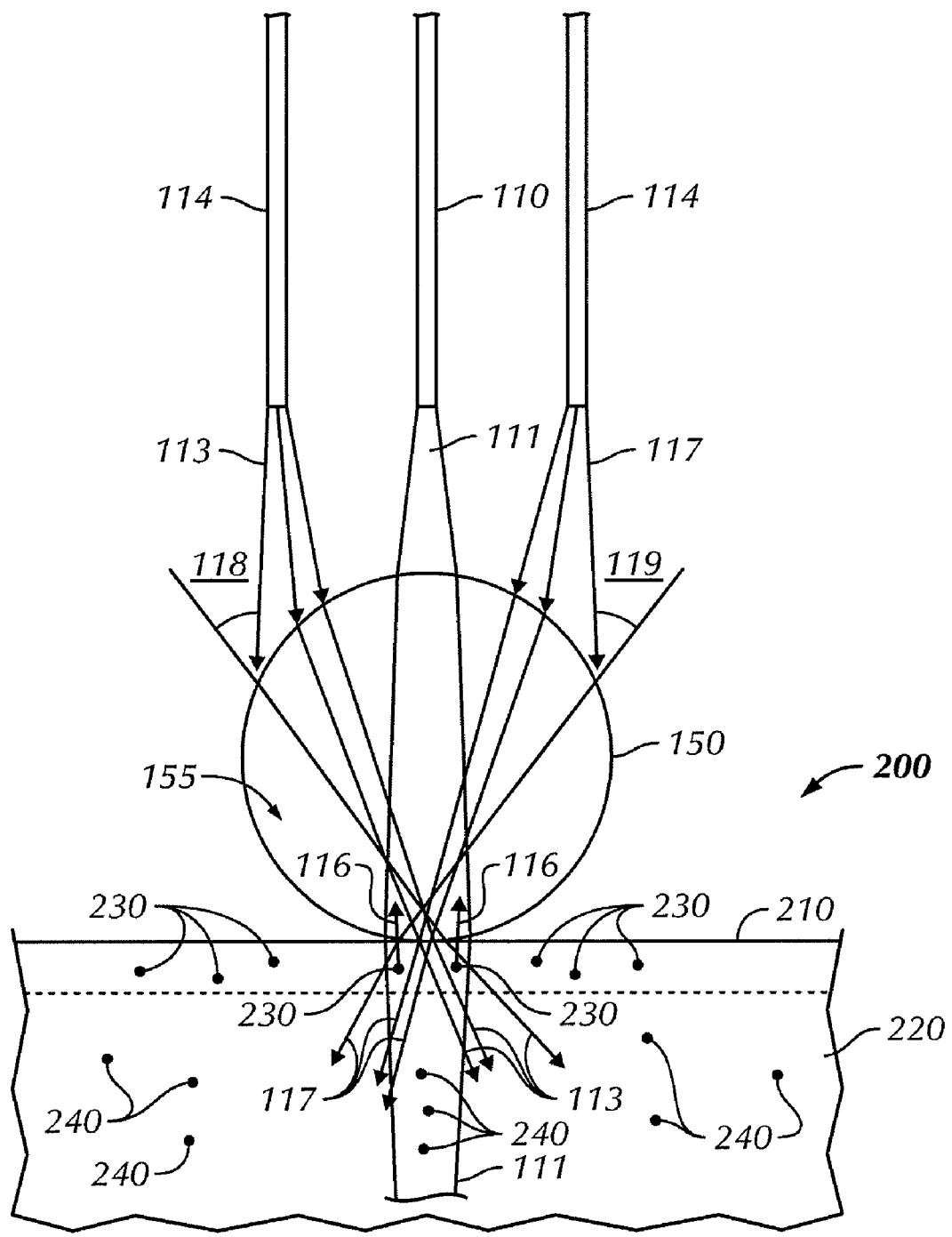
FIG. 4 is a detailed view of a fiber-optic probe and a ball-shaped lens, in accordance with embodiments of this disclosure.

Referring now to FIG. 4, collection fiber 110 and shallow tissue illumination fibers 114 are shown proximal to specimen 200. For purposes of clarity, medium tissue illumination fibers 112 and deep tissue fibers 120, 122, 124, 130, 132 and 134 are not shown in FIG. 4. Specimen 200 comprises a top layer 210 (such as an epithelium) and a supporting layer 220 (such as a stroma). Distributed throughout top layer 210 are a plurality of targets 230 and distributed throughout supporting layer 220 are a plurality of targets 240. As explained previously in this disclosure, it is sometimes desirable to determine the depth of a target 230 or 240 for diagnostic or other purposes.

As shown in FIG. 4, ball-shaped lens 150 refracts a set of light rays 113 and 117 from shallow tissue illumination fibers 114. In addition, ball-shaped lens 150 modifies detection region 111 of collection fiber 110 so that detection region 111 converges, rather than continually diverges. The geometry of collection fiber 110, illumination fibers 114 and ball-shaped lens 150 determines a refraction angle 118 of light rays 113 and a refraction angle 119 of light rays 117. For purposes of clarity, refraction angles 118 and 119 are shown where light rays 113 and 117 enter ball-shaped lens 150. Additional refraction occurs where light rays 113 and 117 exit ball-shaped lens 150. In general, the greater the spacing between collection fiber 110 and shallow tissue illumination fibers 114, the greater the refraction angle.

As shown in the embodiment of FIG. 4, the geometry of fiber-optic probe 100 can be configured so that light rays 113 and 117 intersect detection region 111 in an intersection region 155 that is located proximal to top layer 210. Light rays 113 and 117 then diverge away from detection region 111 in the area just below top layer 210. In this configuration, light rays 113 and 117 are heavily concentrated within top layer 210. In addition, detection region 111 is focused so that light rays 113 and 117 do not significantly intersect detection region 111 in supporting layer 220. Therefore, a target 230 located within top layer 210 and detection region 111 will be illuminated with a greater number of light rays 113 and 117 than a target 240 located in supporting layer 220 and detection region 111. Targets 230 in top layer 210 and detection region 111 will therefore produce a greater number of remitted light rays 116 as compared to targets 240 in supporting layer 220 and detection region 111.

Figure 5:
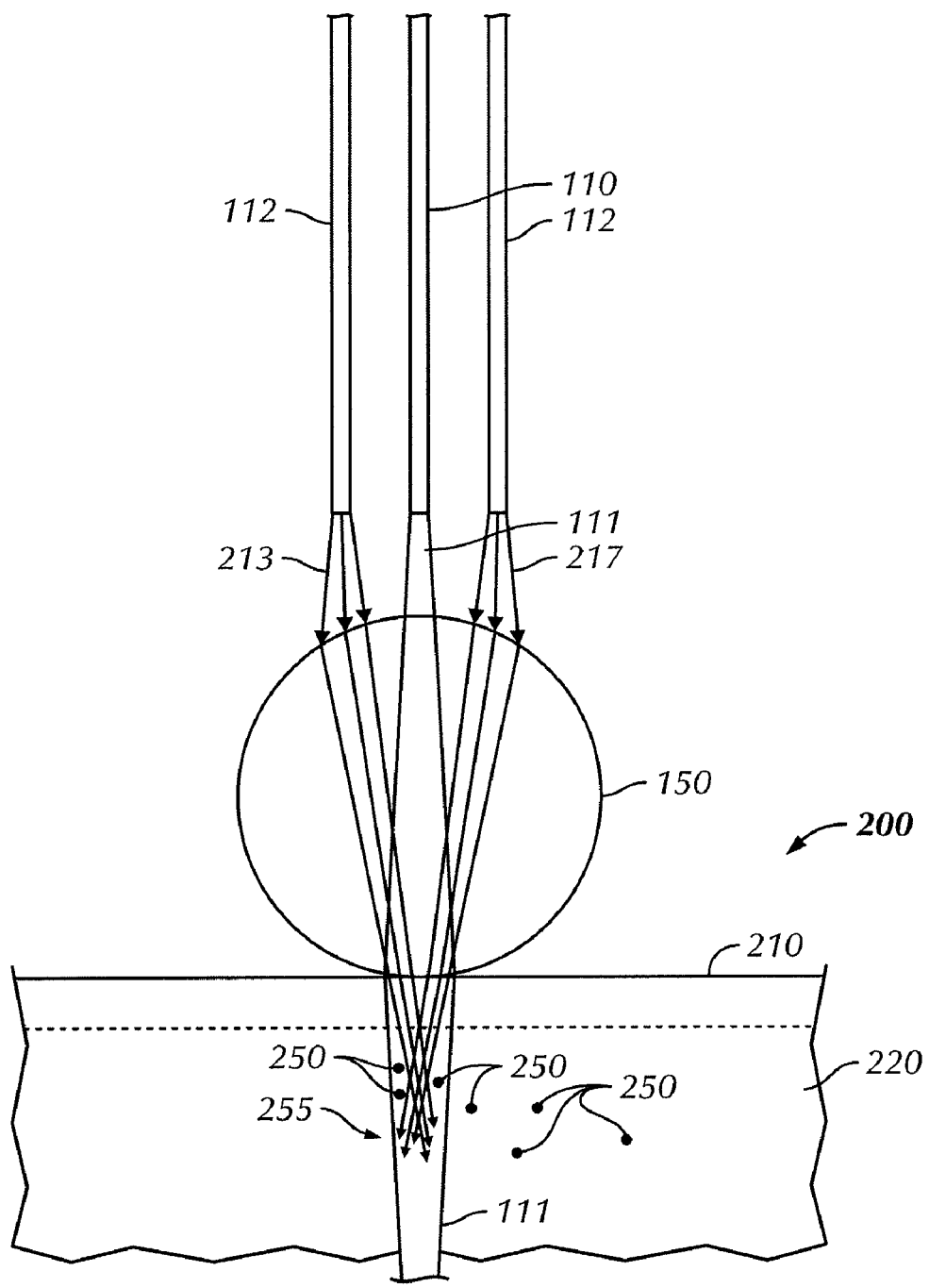
FIG. 5 is a detailed view of a fiber-optic probe and a ball-shaped lens, in accordance with embodiments of this disclosure.

FIG. 5 depicts an arrangement similar to that of FIG. 4, but shows medium tissue illumination fibers 112 instead of shallow tissue illumination fibers 114. Again, deep tissue fibers 120, 122, 124, 130, 132 and 134 are omitted only for the sake of clarity. Embodiments of this disclosure can comprise a fiber-optic probe 100 with any combination of shallow tissue illumination fibers 114, medium tissue illumination fibers 112, or deep tissue illumination fibers (as well as their associated collection fibers). In FIG. 5, medium tissue illumination fibers 112 emit a set of light rays 213 and 217 that are refracted by ball-shaped lens 150 such that light rays 213 and 217 intersect in a medium depth region 255 that is just below top layer 210. In this case, a plurality of targets 250 located in medium depth region 255 will receive the highest number of light rays 213 and 217 and will therefore provide the strongest remission signal.

As previously stated, embodiments of this disclosure may comprise any combination of shallow, medium and deep tissue illumination and collection fibers. In certain embodiments, the wavelength of the illumination light may be sequentially altered depending on the response properties of the targets of interest. In certain embodiments, the shallow, medium and deep tissue fibers can be connected to separate channels that are independently displayed. In such embodiments, the separate channels can be compared to create a spectrographic profile of the specimen. The ability to determine the specific depth region of a target provides an important additional component of information. For example, the ability to determine whether a target producing an optical signature is in the epithelial and/or the stromal layer should improve the ability to evaluate noninvasively the progression of precancerous changes.

Figure 6:
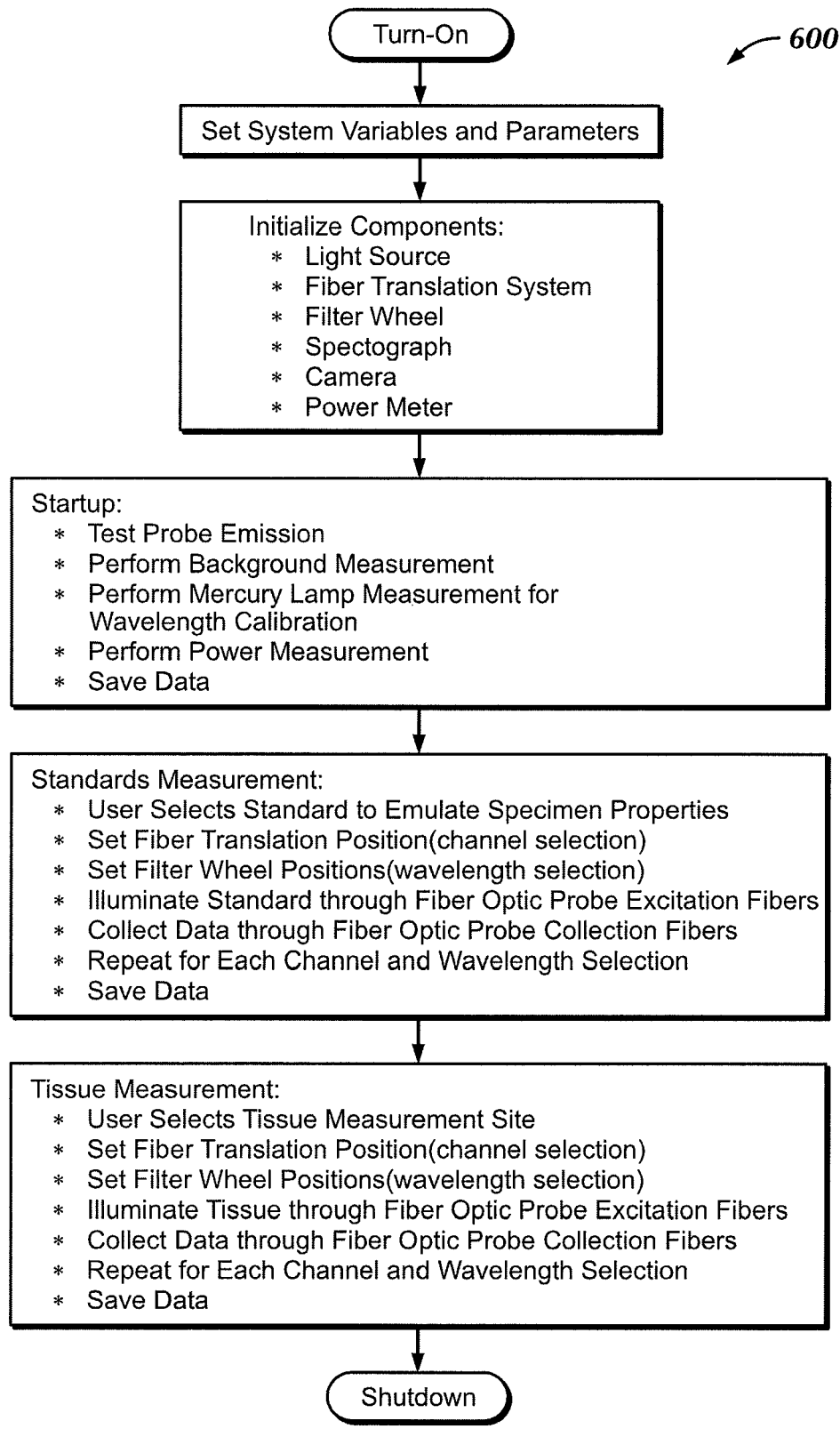
FIG. 6 is a flowchart of steps performed by a software program operating a spectroscopic system, in accordance with embodiments of this disclosure.
Figure 7:
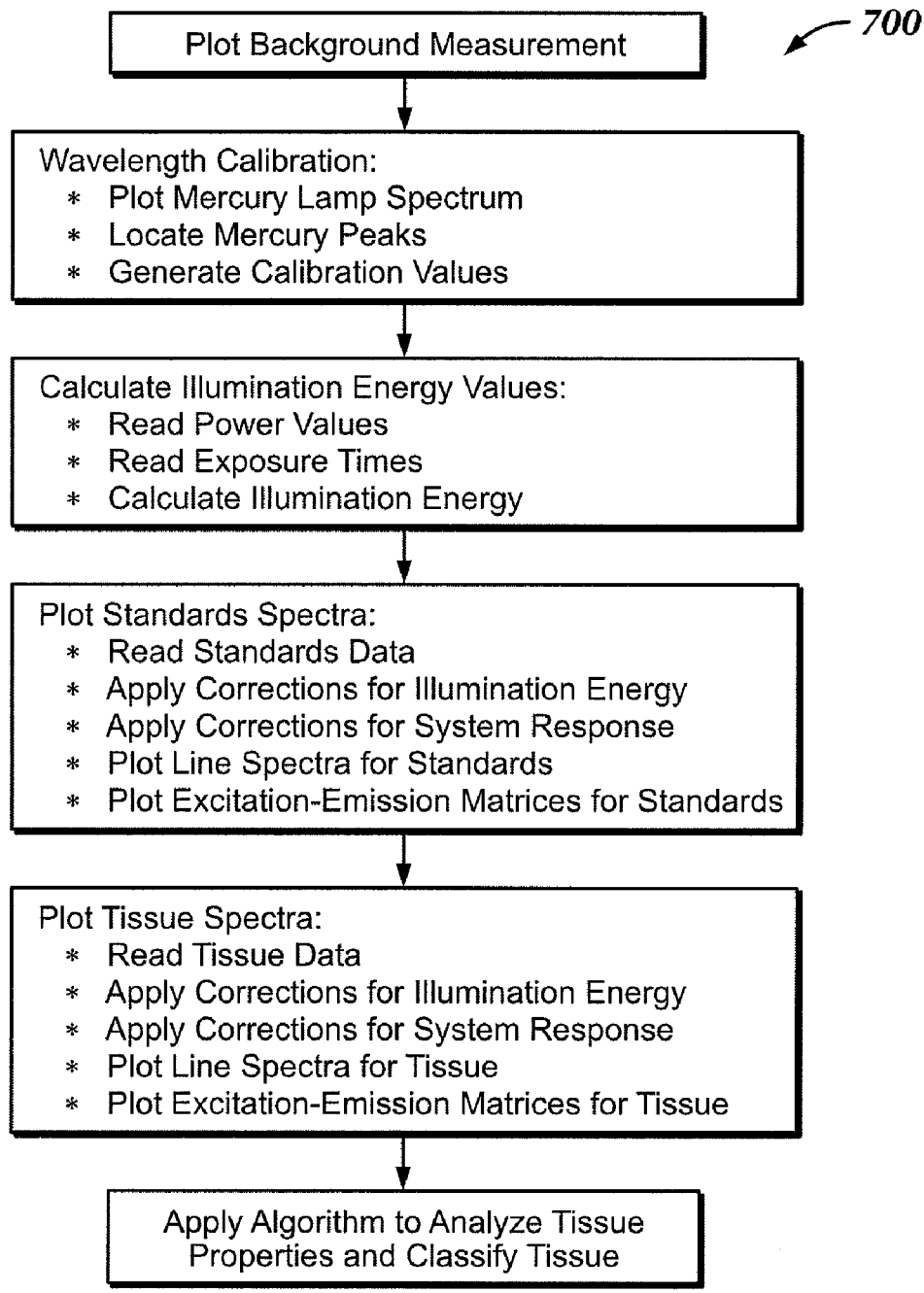
FIG. 7 is a flowchart of steps performed by a software program analyzing data collected by a spectroscopic system, in accordance with embodiments of this disclosure.

During operation, embodiments of the present disclosure may be connected or coupled to a spectroscopic system (not shown) which is operated by a software program. Referring now to FIG. 6, a logic flowchart of one embodiment of such a software program 600 is displayed. A logic flowchart of the analysis of data obtained during operation of the spectroscopic system is shown in FIG. 7.

The software described in this disclosure can be embodied on any computer-readable media known in the art, including but not limited to, hard drives, flash devices, optical drives, etc.

Software Embodiment

1. Introduction

Fast EEM (excitation emission matrix) software is programmed with Labview software, which controls components of a spectroscopic system comprising light sources, a fiber translation system, a filter wheel, a camera and a powermeter. For developing a measuring system, Fast EEM software supports a script engine. The measurement procedure is programmed by script engine.

2. Labview Software
  2.1 Power meter
    (1) 4832-C prepare.vi
    This vi finds the status of 4832 and sets the initial values.
    Step 1: check system (system status and system information) and active channels.
    Step 2: find detector models, calibration date, serial numbers, and attenuator serial numbers.
    Step 3: channel initialize
    Step 4: set initial value
      Responsivity data=>F=calibration Mode, T=user responsivity
      Sample precision=>F=12 bit, T=15 bit
    Step 5: confirm the setting of step 4 by reading the status of power meter.
    Return error code: 5024
    (2) 4832-C setup.vi
    This vi sets the zero state, wavelength, channel range, attenuator, 5 Hz filter and zero state. Only the variables selected by switch cluster are changed, but all state variables are read and checked with global variables. Whenever auto range is selected, which means a channel range value is 7, the power meter's channel range is automatically changed by environment's light, so the returned channel range is different from input value.
    This vi must be called after 4832-C init lowlevel.vi and 4832-C Prepare.vi for the first time.
    Step 1: (If each setting switch is true) set initial values (zero mode, wavelength, channel range, attenuator, 5 Hz filter) if the power meter returns false, setting switches also indicate false.
    Step 2: (If zero meter switch is true) set zero reference (1. 5 Hz on, 2. zero disable, 3. measure watts for zero reference value, 4. set zero when set zero global value is true 5. set 5 Hz filter set as filter set global value)
    Step 3: (Always execution) check the read value from power meter and input value. Read the zero reference.
    Input value: setting switch (Boolean cluster=1. zerostate, 2. wavelength, 3. channel range, 4. attenuator, 5.5 Hz filter),
    Each setting value (Zero state: Boolean array, wavelength: I16 array, Attenuator: Boolean array, 5 Hz filter: Boolean array, Channel Range: I16 array (0, 1, 2, 3, 4, 5, 6, 7 means autorange)
    Power setting switch (Boolean)
    Return value: status value arrays (same format with input variables & auto range status), zero reference value (DBL), error code (5025)
    (3) 4832-C Init lowlevel.vi
    This vi resets the power meter as default values which values were defined by the manufacturing company. This vi must be called at the first time, unless the power meter has a problem.
    Most of the reset values are executed for the interface of between the computer and the powermeter.
    Return value: error code (5023)
    (4) 4832-C Sampling 2Channel data.vi
    This vi measures the 2 channel data (Watts units) of power meter simultaneously and continually during measuring time, every measuring interval time.

Input value: measuring time [seconds] (DBL), measuring interval time [msec](DBL)

Output value: measured data array (DBL), error code (5021) it returns error code, if executed measuring time is more than input measuring time.

(5) 4832-C Sampling 1Channel data.vi

This vi measures the 1 channel data (Watts units) of power meter continually during measuring time, every measuring interval time.

Input value: measuring time [seconds] (DBL), measuring interval time [msec](DBL)

Output value: measured Watts value data array (DBL), error code (5021). it returns error code, if executed measuring time is more than input measuring time.

(6) 4832-c initilaize.vi

This vi resets and initializes the power meter with global values. This vi calls initialize low level.vi 4832-c prepare.vi and 4832-c setup.vi (7) Operate Power meter.vi This vi is based on the program supported from the manufacturing company. This vi can set all environments value and measure all channels data. When this vi is called, it reads and displays the current status of power meter.

(8) Setup Power meter.vi

This vi supports the hardware reset, environment values set, zero meter set, displaying global variables or changing global variables.

Data Cluster 1: base address, channel units, sample precision, and user responsivity.

Data Cluster 2: zero state, wavelength, channel range, attenuator and 5 Hz filter Step 1: Read the global variables and display the front panel.

Step 2: If reset is true,
1. Save front panel's Data cluster 1 and 2 to global variables.
2. Call low initialize sub vi, 4832-C prepare.vi and 4832-C setup.vi Step 3: If operate is true
Call 4832-C operate.c vi Step 4: If initializes is true
1. Save front panel's Data cluster 1 and 2 to global variables.
2. Call 4832-C prepare.vi and 4832-C setup.vi Step 5. If zero meter is true
1. Save only front panel's Data cluster 2 to global variables
2. Call 4832-C setup.vi for setting zero meter.
Zero Meter will also apply 5 Hz input zero mode input to device Step 6: If Ok is true
1. Save only front panel's Data cluster 2 to global variables
2. Call 4832-C setup.vi Step 7: If Display global is true
Replace the front panel's variables as global variables Step 8: If Exit is true
This program is finished.

2.2 Camera (1) AndorMcd Set Camera.vi

This vi sets an image, shutter, and exposure time when each setting switch turns on.

Input: Bin setting switch (Boolean), HorizontalBin (I16), Vertical Bin(I16),
Start Column(I16), EndColumn(I16), Start Row(I16), EndRow(I16)

Shutter setting switch (Boolean), Openshuttersignal(I16, low=0, high=1), shutterMode (I16, auto=0, open=1, close=2)
Exposure time setting switch (Boolean), Exposure time (I16)

Output: Exposure Time Used (SGL)

(2) AndorMcd Dal Acquisition time.vi

This vi calculates the camera data acquisition time.

Total time=shutter transition time×2+Exposure time+Vertical speed×256+Horizontal speed×measuring pixels/bin Input: Exposure time (SGL)
Output: total time (SGL)

2.3 Translation Stage (1) Initialize Translation Stage.vi

This vi initializes the translation stage by calling the initialize 6200 Device.vi and Home Translation Stage.vi (2) Initialize 6200 Device.vi This vi initializes the translation stage and sets environments variables with default variables.

This vi sets the communication between pc and translation, sets 1 axis motion, and enables hardware limit, absolute move position coordination, 25000setp/revolution. This program sets Configure Homming.vi with default values and sets the velocity, accelerates and decelerates with default values.

(3) Home Translation Stage.vi

This vi makes the translation stage move to home position. This program calls Configure Homming.vi (4) Move Translation Stage.vi This vi makes the translation stage move to new position units absolute step.

It calculates the real steps from Set distance.vi supported by the manufacturing company, and commands the go by calling Initiate Motion.vi supported by the manufacturing company.

Input: newposition (DBL)

(5) Select Translation Stage Position.vi

This vi finds the real translation stage position of the selected position ID by reading the table which was read form ini file and save the value to location Scaled, global variable.

This value will be the input value of Move Translation Stage.vi without converting the dimension.

Input: Selected Position (String)
Output: Location (DBL)

(6) Operate Select Translation Position.vi

This vi can move the translation stage to the selected position when set translation switch turns on.

(7) Operate Translation Stage.vi

This vi can move the translation stage to any position, change translation stage moving speed and display the real translation stage position. This is programmed for finding the real translation stage.

Translation stage is moved by step when the forward/backward switch turns on and is moved by 1/10 of step when the forward/backward fine switch turns on. This program can change the speed and can save to global variable when set store speed turns on. This program also can execute the initialize by calling initialize 6200 device.vi and move to home position by calling Home Translation Stage.vi.

(8) Read_variable.vi

This vi returns the translation stage position global variable in table format, which is used in Operate Translation Stage.vi 2.4 Protocol (1) Saveprotocol.vi This vi calls allgoblavaluesave.vi every input second until the stop variable turns on.

This vi makes a filename using the input filename and serial number from 0.

Input: save interval time (DBL) [sec], Stop (Boolean), save path (string), filename (string), (2) Allglobalvaluesave.vi This vi saves all global variables in txt file format, when it is called. This program should be called from main program This vi opens or creates a new text file with the input file name. Because of allocating some memory, it takes much longer time when the first few times of running program.

Input: the save filename (string)

2.5 Matlab

Call matlab funcution.vi

This vi executes the matlab function command and returns the matlab function result. When this program is called, the matlab program is executed automatically.

Input: matlab command (string)

Output: return of matlab command (I32)

3. File Saving Structure

Script engine generates the data file at the specific directory as like these. In the below, some variables which are used at script engine for data saving are explained. Software changes include from: FastEEM v0.4.1 (used for FastEEM 3) to: FastEEM4 v1.0 (used for FastEEM 4).

Following are the modifications made to FastEEM v0.4.1 to generate FastEEM4 v1.0. The software had to be changed because FastEEM v0.4. 1 has four 12 position filter wheels and FastEEM4 v1.0 has three 10 position filter wheels.

Fast EEM.ini

Removed:

Wheel 4=3

Power 4=ON

Speed 4=3

Folder: Main

VI: Readini.vi

Lambda 12 cont 2—changed 4 to 3

Lambda 12 cont 3—changed 4 to 3

Lambda 12 cont 4—changed 4 to 3

Filter selection: changed 5 to 4

Folder: Filters

VI: Lambda 12 change Spx Wheel.vi\

Changed from:

0, 0, 0, 1

To:

0, 0, 1, 0

Removed the last row with the zero to get rid of the fourth wheel assignment.

Folder: Filters

VI: Lambda 12 initialize Serial port.vi

Changed from:

131, 147, 163, 179

To:

131, 147, 163

Folder: Filters

VI: Lambda12 serial comm (in series).vi

Removed:

Wheel 4 commands

Folder: Filters

VI: Lambda 12 change wavelength.vi

Changed from:

1, 1, 1, 1

To:

1, 1, 1, 0

Removed the last row with the zero to get rid of the fourth wheel assignment.

Folder: Filter

VI: Lambda 12 get status.vi

Send request to controller: 1. [0.3]

Removed:

Wheel 4 commands

Get response 2. [0.3]

Deleted case with wheel 4 commands

Changed the number next to the case structure from 4 to 3.

Folder: Filters

VI: Lambda 12 setup.vi:

Outer case [0[0.1]]—initialize

Inner case [2[0.2]]

Changed loop value from 4 to 3

Removed the fourth case with the wheel 4 controls.

Outer case [1. [0.1]]—change globals and operate

Inner case [8. [0.10]]—exit and execute global

Changed from:

1, 1, 1, 1

To:

1, 1, 1, 0

Removed the last row with the zero to get rid of the fourth wheel assignment

Folder: Filters

VI: Lambda 12 change Spx wheel vi

Changed array value from 3 to 2, which makes wheel 3 the spx wheel instead of wheel four.

In the front panel, removed the 10th and 11th positions on the SPX wheel filter selection using the delete element option. After making a new set of filter assignment in the FAST EEM ini file. The following changes were made in the labview program.

Folder—Main

VI: readini.vi

Filter selection: changed from 39 to 26

Operate All:

To get rid of the position 10 and 11 in the operate all Spx wheel selection; simply delete the position 10 and 11 using the delete element option.

Camera Modifications Made to the Original Lab View Software:

Fast EEM.ini

Section: [Andor MCD]

Changed end row from 256 to 255

Changed start row from 1 to 2

Non VI's File changes:

Folder: Camera

Atmcd 32d.dll

Detector.ini

Pci_29k.cof

Pci_fpga.rbf

The disclosure and claims should not be limited to the specific preferred or other embodiments described above. For example, even a preferred embodiment is meant simply as an example to help illuminate for the reader one or more techniques being described. With the benefit of the present disclosure, those having ordinary skill in the art will comprehend that techniques claimed here and described above may be modified and applied to a number of additional, different applications, achieving the same or a similar result. The attached claims cover all such modifications that fall within the scope and spirit of this disclosure.

REFERENCES

Each of the following references is hereby incorporated by reference in its entirety:
U.S. Pat. No. 5,974,211
"Ball lens coupled fiber-optic probe for depth-resolved spectroscopy of epithelial tissue" by Richard A. Schwarz, et. al, *Optics Letters*, Vol. 30, No. 10, May 15, 2005
"Optical fiber probe for biomedical Raman spectroscopy" by Jason T. Motz, et. al, *Applied Optics*, Vol. 43, No. 3 Jan. 20, 2004
"Fiber Optic Probes for Biomedical Optical Spectroscopy," by U. Utzinger and R. Richards-Kortum, *Journal of Biomedical Optics*, Vol. 8, No. 1, January 2003, pp. 121-147.

The invetion claimed is:

1. A method of obtaining spectroscopic data from a target in a specific depth layer of a specimen, comprising:
   providing a fiber-optic probe comprising:
      a first excitation source emitting a first output light;
      a collection fiber configured to receive an optical signal in a detection region;
      an end; and
      a ball lens proximal to the end, wherein the ball lens has a central axis and the collection fiber is proximal to the central axis;
   locating the fiber-optic probe such that the ball lens is proximal to the specimen;
   redirecting the first output light with the ball-shaped lens, wherein:
      the first output light intersects the detection region in the specific depth layer of the specimen; and
      the first output light illuminates the target, wherein the target is located both in the specific depth layer of the specimen and in the detection region;
   generating the optical signal from the target; and
   receiving the optical signal in the collection fiber.

2. The method of claim 1 further comprising the steps of:
   providing a second excitation source emitting a second output light;
   redirecting the second output light with the ball-shaped lens, wherein:
      the second output light intersects the detection region in the specific depth layer of the specimen; and
      the second output light illuminates the target.

3. The method of claim 2, wherein the first excitation source and the second excitation source are parallel fiber-optic illumination fibers.

4. The method of claim 3, wherein the first excitation source and the second excitation source are equidistant from the collection fiber.

5. The method of claim 1, wherein the ball lens is in contact with the specimen.

6. The method of claim 1, wherein the specific depth layer is an epithelial layer of an organ.

7. The method of claim 1, wherein the target is a chromophore.

8. The method of claim 1, wherein the first excitation source is separated from the collection fiber by approximately 0.5 millimeters.

9. The method of claim 1, further comprising the step of:
   evaluating the optical signal to determine if the target is pre-cancerous or cancerous.

10. The method of claim 1, further comprising the step of:
    selecting a spacing between the first excitation source and the collection fiber so that the first output light intersects the detection region in the depth layer near the surface of the specimen.

11. A method of obtaining spectroscopic data from a target in a specific depth region of a specimen, comprising:
    providing a fiber-optic probe comprising:
       a first illumination fiber;
       a collection fiber configured to receive a set of light rays in a detection region;
       an end; and
       a ball-shaped lens proximal to the end, where the ball-shaped lens has a central axis and the collection fiber is proximal to the central axis;
    locating the fiber-optic probe such that the ball-shaped lens is proximal to the specimen;
    emitting a first set of excitation light rays from the first illumination fiber, where:
       the first set of excitation light rays are refracted by the ball-shaped lens to illuminate the target in the specific depth region of the specimen;
       the first set of excitation light rays intersect the detection region in the specific depth region of the specimen; and
       the first set of excitation light rays produce a first set of remitted light rays from the target in the specific depth region; and
    receiving the first set of remitted light rays in the collection fiber.

12. The method of claim 11, further comprising the steps of:
provide a second illumination fiber;
emitting a second set of excitation light rays from the second illumination fiber, where:
the second set of excitation light rays are refracted by the ball-shaped lens to illuminate the target in the specific depth region of the specimen;
the second set of excitation light rays intersect the detection region in the specific depth region of the specimen; and
the second set of excitation light rays produce a second set of responsive remitted light rays from the target in the specific depth region; and
receiving the second set of responsive remitted light rays in the collection fiber.

13. The method of claim 12, wherein the second set of excitation light rays intersect the first set of excitation light rays proximal to a distal surface of the ball-shaped lens.

14. The method of claim 11, wherein the specific depth region is near the surface of the specimen.

15. The method of claim 11, wherein one of the illumination fibers is separated from the collection fiber by approximately 0.5 millimeters.

16. An optical probe comprising:
a fiber optic cable comprising:
an end;
a collection fiber configured to receive a set of light rays in a detection region; and
a first pair of illumination fibers configured to emit a first set of excitation light rays; and
a ball-shaped lens having a central axis, where:
the ball-shaped lens is proximal to the end of the fiber optic cable;
the collection fiber is proximal to the central axis;
each of the illumination fibers are distal to the central axis;
the ball-shaped lens is configured to modify the detection region of the collection fiber to include a convergent portion; and
the ball-shaped lens is configured to refract the first set of excitation light rays so that the first set of excitation light rays intersect the detection region in a first section of the convergent portion.

17. The probe of claim 16, where each of the illumination fibers are equidistant from the collection fiber.

18. The probe of claim 16, where each of the illumination fibers emit light rays that are refracted by the ball-shaped lens.

19. The probe of claim 18, where the light rays emitted by one illumination fiber intersect the light rays emitted by the other illumination fiber at an intersection region.

20. The probe of claim 18, where a portion of the intersection region is located on an outer surface of the ball-shaped lens.

21. The probe of claim 20, further comprising a second set of illumination fibers configured to emit a second set of excitation light rays, where:
the ball-shaped lens is configured to refract the second set of excitation light rays so that the second set of excitation light rays intersect the detection region in a second section of the convergent portion of the detection region; and
the second section of the convergent portion of the detection region is farther from the ball-shaped lens than is the first section of the convergent portion of the detection region.

22. The probe of claim 16, where one of the illumination fibers is separated from the collection fiber by approximately 0.5 millimeters.

* * * * *

UNITED STATES PATENT AND TRADEMARK OFFICE
CERTIFICATE OF CORRECTION

PATENT NO. : 7,499,161 B2  Page 1 of 1
APPLICATION NO. : 11/428806
DATED : March 3, 2009
INVENTOR(S) : Rebecca Richards-Kortum et al.

It is certified that error appears in the above-identified patent and that said Letters Patent is hereby corrected as shown below:

In column 1, line 11, insert the following paragraph
--This invention was made with government support under CA095604 awarded by the National Institutes of Health. The government has certain rights in the invention.--.

Signed and Sealed this

Twelfth Day of May, 2009

JOHN DOLL
*Acting Director of the United States Patent and Trademark Office*